US008859807B2

(12) United States Patent
Sakai et al.

(10) Patent No.: US 8,859,807 B2
(45) Date of Patent: Oct. 14, 2014

(54) GLUTATHIONE PREPARATION AND METHOD FOR PRODUCTION THEREOF

(75) Inventors: Yasushi Sakai, Tsukuba (JP); Aki Kato, Tsukuba (JP); Masao Kimura, Tsukuba (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 806 days.

(21) Appl. No.: 12/444,298

(22) PCT Filed: Oct. 4, 2007

(86) PCT No.: PCT/JP2007/069433
§ 371 (c)(1),
(2), (4) Date: Apr. 3, 2009

(87) PCT Pub. No.: WO2008/041740
PCT Pub. Date: Apr. 10, 2008

(65) Prior Publication Data
US 2010/0048948 A1    Feb. 25, 2010

(30) Foreign Application Priority Data
Oct. 4, 2006  (JP) ................................. 2006-272668

(51) Int. Cl.
*C07C 323/39*  (2006.01)
*A61K 47/18*  (2006.01)
*A61K 38/06*  (2006.01)

(52) U.S. Cl.
CPC .............. *A61K 47/183* (2013.01); *A61K 38/063* (2013.01)
USPC ............................ 562/556; 562/560; 562/565

(58) Field of Classification Search
None
See application file for complete search history.

(56) References Cited

U.S. PATENT DOCUMENTS

| 2,851,482 A | * | 9/1958 | Barker et al. ................. 562/560 |
| 3,482,025 A | * | 12/1969 | Kawashima et al. ......... 514/419 |
| 5,895,658 A | * | 4/1999 | Fossel ............................ 424/401 |
| 6,323,211 B1 | * | 11/2001 | Garvey et al. ................. 514/280 |

FOREIGN PATENT DOCUMENTS

| JP | 47-25312 A | | 10/1972 | |
| JP | 57-112367 | * | 7/1982 | .......... C07C 149/243 |
| JP | 64-63342 A | | 3/1989 | |
| JP | 05-176739 A | | 7/1993 | |
| JP | 06-78713 A | | 3/1994 | |
| JP | 2002-97153 A | | 4/2002 | |
| WO | WO8402274 A1 | * | 6/1984 | ............. A61K 35/12 |
| WO | WO 2006/106805 A | | 10/2006 | |
| WO | WO 2006/106806 A | | 10/2006 | |
| WO | WO2006106805 | * | 10/2006 | ........... A61K 31/375 |

OTHER PUBLICATIONS

English abstract of JP 57-112367, published Jul. 1982.*
English language translation of JP 57112367, published Jul. 1982.*
Bilton, Gerald L., Activated, stabilized enzymes useful for wound healing, Jun. 1984, WO 8402274, abstract.*
Cas Registry No. 4320-30-3, obtained Mar. 11, 2014, pp. 1-2.*
Jiten, *Kabushiki Kaisha Yakuji Nipposha*, 1: 22-23 and 44-45 (1994).

\* cited by examiner

*Primary Examiner* — Rosalynd Keys
(74) *Attorney, Agent, or Firm* — Leydig, Voit & Mayer, Ltd.

(57) ABSTRACT

The present invention relates to a method of improving the preservation stability of glutathione, which is characterized by allowing glutathione to co-exist with an arginine-acidic amino acid salt. In addition, the present invention relates to a production method of a glutathione preparation, which is characterized by mixing glutathione and an arginine-acidic amino acid salt. By the production method, a glutathione preparation that resists quality deterioration can be provided. Moreover, the present invention relates to a preservation method of glutathione, which is characterized by allowing glutathione to co-exist with an arginine-acidic amino acid salt. By the preservation method, quality deterioration of glutathione during preservation can be suppressed.

12 Claims, No Drawings

GLUTATHIONE PREPARATION AND METHOD FOR PRODUCTION THEREOF

CROSS-REFERENCE TO RELATED APPLICATIONS

This patent application is the U.S. national phase of International Patent Application No. PCT/JP2007/069433, which was filed on Oct. 4, 2007, and which claims priority to Japanese Patent Application No. 272668/2006, filed on Oct. 4, 2006.

TECHNICAL FIELD

The present invention relates to a method of improving the preservation stability of glutathione, a glutathione preparation and a production method thereof, as well as a preservation method of glutathione.

BACKGROUND ART

Glutathione is a substance frequently utilized for pharmaceutical agents and health foods since it has various physiological activities. The substance itself is generally an odorless powder. However, an unpleasant odor like sulfur may be developed due to the influence of heat, oxygen, light and the like during preservation in the form of a powder or a preparation containing glutathione as a main component, i.e., a glutathione preparation. In some cases, glutathione content in the preparation is lowered; consequently, the quality of glutathione is deteriorated.

As a method of suppressing deterioration of the quality of glutathione during preservation, i.e., a method of improving the preservation stability of glutathione, a method including coating the surface of the particles of a glutathione powder (see patent documents 1 and 2), a method including adding cyclodextrin (see patent documents 3 and 4) and the like are known.

However, these methods are problematic in that the operation is complicated and a sufficient effect cannot be obtained.

In view thereof, the development of a glutathione preparation that resists quality deterioration and a preservation method of glutathione that resists quality deterioration has been desired.

patent document 1: JP-A-5-176739
patent document 2: JP-A-2002-97153
patent document 3: JP-A-64-63342
patent document 4: JP-A-6-78713

DISCLOSURE OF THE INVENTION

Problems to be Solved by the Invention

An object of the present invention is to provide a method of improving the preservation stability of glutathione, a glutathione preparation that resists quality deterioration, a production method of the preparation, or a preservation method of glutathione that resists quality deterioration.

Means of Solving the Problems

The present invention relates to the following (1) to (4).
(1) A method of improving the preservation stability of glutathione, which comprises allowing glutathione to co-exist with an arginine-acidic amino acid salt.
(2) A method of producing a glutathione preparation, which comprises a step of mixing glutathione and an arginine-acidic amino acid salt.
(3) A glutathione preparation comprising glutathione and an arginine-acidic amino acid salt.
(4) A method of preserving glutathione, which comprises allowing glutathione to co-exist with an arginine-acidic amino acid salt.

Effect of the Invention

According to the present invention, a method of improving the preservation stability of glutathione, a glutathione preparation that resists quality deterioration, a production method of the preparation, or a preservation method of glutathione that resists quality deterioration can be provided.

BEST MODE FOR CARRYING OUT THE INVENTION

In the method of improving the preservation stability of glutathione of the present invention, glutathione is allowed to co-exist with an arginine-acidic amino acid salt by, for example, a method comprising contacting glutathione with an arginine-acidic amino acid salt such as a method comprising mixing glutathione and an arginine-acidic amino acid salt.

Glutathione may be any of a reduced form (L-γ-glutamyl-L-cysteinylglycine) and an oxidized form (glutathione disulfide).

Glutathione may be any of a powder, a particulate and a mixture thereof, or may be contained in a product containing glutathione such as a yeast extract and the like. The water content is preferably not more than 5 wt %, more preferably not more than 3 wt %.

Arginine acid in the arginine-acidic amino acid salt may be any of an L form and a D form, with preference given to an L form.

Examples of the acidic amino acid salt in the arginine-acidic amino acid salt include glutamate and aspartate.

The arginine-acidic amino acid salt may be any of a powder, a particulate and a mixture thereof. The water content is preferably not more than 3 wt %, more preferably not more than 1 wt %, and still more preferably not more than 0.3 wt %.

The amount of the arginine-acidic amino acid salt to be allowed to co-exist with glutathione is preferably 0.1-1,000 parts by weight, more preferably 1-500 parts by weight, and still more preferably 2-200 parts by weight, per 1 part by weight of glutathione.

When glutathione and an arginine-acidic amino acid salt are allowed to co-exist, a substance generally used in the field of pharmaceutical product, food or feed, which does not adversely influence improvement of the preservation stability of glutathione, may be further added.

Examples of the substance generally used in the field of pharmaceutical product, food or feed include base for preparations such as excipient, disintegrant, binder, lubricant and the like, sweetener, acidulant, colorant, flavor, antioxidant, fluidizer and the like.

Examples of the excipient include maltose, trehalose, mannitol, hydrogenated maltose starch syrup, lactitol, xylitol, sorbitol, erythritol, crystalline cellulose, low-substituted hydroxypropylcellulose and the like.

Examples of the disintegrant include carboxymethylcellulose, calcium carboxymethylcellulose, sodium carboxymethylcellulose, crospovidone, croscarmellose sodium, sodium glycolate, starch such as cornstarch, potato starch, partly pregelatinized starch and the like, and the like.

Examples of the binder include polyvinylpyrrolidone, pullulan, methylcellulose, hydroxypropylcellulose, polyvinyl alcohol, gelatin, agar and the like.

Examples of the lubricant include stearic acid or metal salt thereof such as stearic acid, magnesium stearate, calcium stearate and the like, sucrose fatty acid ester, glycerol fatty acid ester, hydrogenated fats and oils, silicon dioxide, calcium phosphate and the like.

Examples of the sweetening agent include saccharin sodium, dipotassium glycyrrhizinate, aspartame, stevia, thaumatin, sucralose, glucose, fructose, saccharose and the like.

Examples of the acidulant include citric acid, tartaric acid, malic acid and the like.

Examples of the colorant include Food Color Yellow No. 5, Food Color Red No. 2, Food Color Blue No. 2, carotenoid pigment, tomato pigment and the like.

Examples of the flavor include lemon flavor, lemon-lime flavor, grapefruit flavor, apple flavor, orange flavor and the like.

Examples of the antioxidant include ascorbic acid, tocopherol, cysteine hydrochloride, L-ascorbyl stearate and the like.

Examples of the fluidizer include calcium phosphate, calcium hydrogen phosphate, colloidal silicon dioxide and the like.

In addition to those mentioned above, saccharides other than the saccharides exemplified as the sweetener in the above such as xylose, galactose, trehalose, lactose, palatinose, maltitol, erythritol, sorbitol, xylitol, raffinose, inulo-oligosaccharide (chicory oligosaccharide), palatinose oligosaccharide and the like, vitamins such as niacin, vitamin A, vitamin B, vitamin D and the like, minerals such as sodium and the like, desiccant or anticaking agent such as colloidal silicon dioxide, calcium silicate, synthetic aluminum silicate, talc and the like, and the like may also be used.

When these substances are allowed to co-exist, they preferably coexist without being dissolved in a solvent such as an aqueous solvent (e.g., water, aqueous inorganic salt solution, buffer and the like), alcohol (e.g., methanol, ethanol, glycerol and the like), or a mixture thereof and the like.

When these substances are allowed to co-exist by mixing, the water content of the obtained mixture preferably does not exceed 5 wt %, more preferably 3 wt %.

By allowing glutathione to co-exist with an arginine-acidic amino acid salt in this way, the preservation stability of glutathione can be improved, and the deterioration of the quality of glutathione during preservation can be suppressed.

As a preservation method of glutathione, other than coexistence with an arginine-acidic amino acid salt, an ordinary preservation method of glutathione including placing glutathione coexistent with an arginine-acidic amino acid salt in a suitable container and the like, shading the container as necessary, keeping the container at low temperature and low humidity and the like can be employed.

The percentage of glutathione amount after preservation to that before preservation, i.e., glutathione residual ratio, can be used as an index of the preservation stability of glutathione.

The glutathione preparation of the present invention contains glutathione and an arginine-acidic amino acid salt and, where necessary, a base for preparation, which is used in the field of pharmaceutical products or food.

The water content of the glutathione preparation of the present invention is preferably not more than 5 wt %, more preferably not more than 3 wt %.

The glutathione preparation of the present invention is preferably in the form of a solid preparation, for example, powder, granule, tablet, capsule and the like.

The glutathione preparation of the present invention can be produced using a composition obtained by allowing glutathione to co-exist with an arginine-acidic amino acid salt and, where necessary, a base for preparation, which is used in the field of pharmaceutical products or food, in the above-mentioned method of improving the preservation stability of glutathione, preferably a mixture thereof, as a preparation starting material according to a general preparation method of solid preparations.

For example, a powder can be produced by mixing powdery preparation starting materials in a mixing machine, or grinding the preparation starting materials in a grinding machine and the like, and mixing them in a mixing machine and the like.

Granule can be produced by granulating the preparation starting materials in a granulating machine.

Tablet can be produced by tableting preparation starting materials in a tableting machine.

After formulation, granule and tablet may be subjected to sugar coating using sugar, sugar alcohol and the like, film coating using a polymer, and the like.

Capsule can be produced by preparing a powder or granules and filling same in a hard capsule.

In addition to the above, solid preparations such as pill, troche, microcapsule and the like may be prepared according to a conventional method.

The content of glutathione and arginine-acidic amino acid salt in the glutathione preparation of the present invention is preferably 30-100 wt %, more preferably 40-80 wt %.

The glutathione preparation of the present invention can be utilized in the field of pharmaceutical product, food or feed. For ingestion by a human or non-human animal, 50 mg-10 g of glutathione is preferably ingested per day.

Example 1

L-arginine L-glutamate (manufactured by Kyowa Hakko Kogyo Co., Ltd., hereinafter to be referred to as arginine-glutamate) was heated at 70° C. for 1 hr. The obtained arginine-glutamate (5 g) and glutathione (1 g, manufactured by Kyowa Hakko Kogyo Co., Ltd., hereinafter the same) were mixed to give powder A.

By an operation similar to that for the production of powder A except that arginine, maltitol and mannitol were used instead of arginine•glutamate, powders B, C and D were respectively produced. Maltitol and mannitol are substances frequently used as excipients.

The water content of each of powders A-D was not more than 0.5%.

For an acceleration test, 50 μl of water was added dropwise to each of powders A-D, they were mixed and placed in an aluminum pouch, which was tightly sealed and preserved at 40° C.

A small amount was sampled from the aluminum pouch at one day and 7 days after the start of the preservation, and subjected to a sensory evaluation of powdery state and odor by 5 panelists.

The test of powder B was stopped since it developed an unpleasant odor and solidification of powder occurred on day 1 after the start of the preservation.

The results are shown in Table 1.

TABLE 1

|  | addition to glutathione | solidification | | Uncomfortable odor | |
| --- | --- | --- | --- | --- | --- |
|  |  | 1 day later | 7 days later | 1 day later | 7 days later |
| powder A | arginine• glutamate | absent | absent | absent | absent |
| powder B | arginine | present | test stopped | present* | test stopped |

TABLE 1-continued

| | addition to glutathione | solidification 1 day later | solidification 7 days later | Uncomfortable odor 1 day later | Uncomfortable odor 7 days later |
|---|---|---|---|---|---|
| powder C | maltitol | absent | absent | absent | present* |
| powder D | mannitol | absent | somewhat present | absent | present* |

*recognized by all five panelists

As shown in Table 1, powder A containing arginine glutamate did not develop an unpleasant odor even after preservation for one week, and the powdery state did not change.

Example 2

The respective components shown in Table 2 were sufficiently mixed in a polyethylene bag to give powders E and F. Glutathione and arginine-acidic amino acid salt used were those prepared in Example 1.

The prepared powders E and F were tightly sealed in aluminum-deposited bags, and preserved for 3 months in a thermostatic tank at 40° C. After preservation, the aluminum-deposited bags were opened, and subjected to a sensory evaluation of odor of the powder by 5 panelists.

As a result, all five panelists evaluated powder F to have a clear unpleasant odor.

TABLE 2

| | powder E | powder F |
|---|---|---|
| Glutathione (1) | 25 | 25 |
| arginine glutamate (2) | 60 | — |
| maltitol | — | 60 |
| microcrystalline cellulose (3) | 10 | 10 |
| sugar ester | 5 | 5 |

(1), (2): manufactured by Kyowa Hakko Kogyo Co., Ltd.
numerical value in wt %
(3): manufactured by Asahi Chemical Industry Co., Ltd.

Example 3

Powders E and F prepared in Example 2 were each compression-molded using a one-shot-type compression molding machine to give tablets (diameter 8 mm, 240 mg).

Each tablet was tightly sealed in an aluminum-deposited bag, and preserved for 3 months in a thermostatic tank at 40° C. After preservation, a sensory evaluation of the odor of the tablet was performed. As a result, all five panelists evaluated the tablet obtained using powder F to have a more unpleasant odor.

Example 4

A mixture of a yeast extract containing glutathione (manufactured by Kyowa Hakko Kogyo Co., Ltd.), arginine-glutamate, granulated sugar, citric acid and trehalose is granulated using a 5% aqueous pullulan solution in a fluid bed granulator. The obtained granules are mixed with a sweetener, a vanilla flavor and ascorbic acid to give vanilla flavored granules.

INDUSTRIAL APPLICABILITY

According to the present invention, a method of improving the preservation stability of glutathione, a glutathione preparation that resists quality deterioration, a production method of the preparation, or a preservation method of glutathione that resists quality deterioration can be provided.

The invention claimed is:

1. A method of improving the preservation stability of glutathione in a solid glutathione preparation, which comprises allowing glutathione to co-exist with an arginine-acidic amino acid salt, wherein the arginine-acidic amino acid salt consists of the amino acid salt of arginine and glutamate.

2. A method of producing a solid glutathione preparation, which comprises a step of mixing glutathione and an arginine-acidic amino acid salt, wherein the arginine-acidic amino acid salt consists of the amino acid salt of arginine and glutamate.

3. A solid glutathione preparation comprising glutathione and an arginine-acidic amino acid salt, wherein the arginine-acidic amino acid salt consists of the amino acid salt of arginine and glutamate.

4. A method of preserving glutathione in a solid glutathione preparation, which comprises allowing glutathione to co-exist with an arginine-acidic amino acid salt, wherein the arginine-acidic amino acid salt consists of the amino acid salt of arginine and glutamate.

5. The method of claim 1, wherein the glutathione has a water content of not more than 5 wt %, and wherein the arginine-acidic amino acid salt has a water content of not more than 3 wt %.

6. The method of claim 5, wherein the glutathione preparation has a water content of not more than 5 wt %.

7. The method of claim 2, wherein the glutathione has a water content of not more than 5 wt %, and wherein the arginine-acidic amino acid salt has a water content of not more than 3 wt %.

8. The method of claim 7, wherein the glutathione preparation has a water content of not more than 5 wt %.

9. The preparation of claim 3, wherein the glutathione has a water content of not more than 5 wt %, and wherein the arginine-acidic amino acid salt has a water content of not more than 3 wt %.

10. The preparation of claim 9, wherein the glutathione preparation has a water content of not more than 5 wt %.

11. The method of claim 4, wherein the glutathione has a water content of not more than 5 wt %, and wherein the arginine-acidic amino acid salt has a water content of not more than 3 wt %.

12. The method of claim 11, wherein the glutathione preparation has a water content of not more than 5 wt %.

* * * * *